United States Patent [19]

Hwang et al.

[11] Patent Number: 5,068,180
[45] Date of Patent: Nov. 26, 1991

[54] SUBSTRATES FOR BETA-GALACTOSIDASE

[75] Inventors: Deng R. Hwang, Tarrytown, N.Y.; Mary Ellen A. Scott, Ringwood, N.J.

[73] Assignee: Technicon Instruments Corporation, Tarrytown, N.Y.

[21] Appl. No.: 433,426

[22] Filed: Nov. 8, 1989

Related U.S. Application Data

[63] Continuation of Ser. No. 52,328, May 21, 1987, abandoned.

[51] Int. Cl.$^5$ .................. G01N 33/53; G07G 3/00; C07H 15/00; C12Q 1/54
[52] U.S. Cl. .................. 435/7.92; 435/793; 435/794; 435/14; 435/18; 536/4.1; 536/17.7; 536/18.4
[58] Field of Search ............ 435/7.92–7.94, 435/14, 18; 536/17.2, 17.6, 17.7, 17.8, 18.1, 18.4, 4.1

[56] References Cited

U.S. PATENT DOCUMENTS

| | | | |
|---|---|---|---|
| 4,145,527 | 3/1979 | Burns et al. | 536/4 |
| 4,668,622 | 5/1987 | Kuhr et al. | 435/14 |
| 4,716,222 | 12/1987 | Wallenfels et al. | 536/18.7 |

FOREIGN PATENT DOCUMENTS

| | | | |
|---|---|---|---|
| 0180961 | 5/1986 | European Pat. Off. | 435/14 |
| 1177999 | 8/1986 | Japan | 435/18 |

OTHER PUBLICATIONS

Dale et al, Biochemistry, vol. 25(9), 1986, pp. 2522–2529.

Primary Examiner—Esther L. Kepplinger
Assistant Examiner—Jacintha M. Stall
Attorney, Agent, or Firm—Jeffrey M. Greenman

[57] ABSTRACT

A substrate for β-galactosidase having the general formula

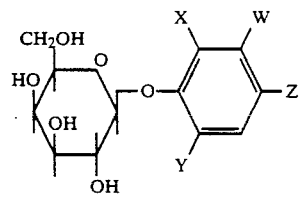

wherein X is halogen; Y is halogen, lower alkyl or hydrogen; W is lower alkyl or hydrogen; and Z is nitro.

18 Claims, 3 Drawing Sheets

SUBSTRATES FOR BETA-GALACTOSIDASE

This is a continuation of co-pending application Ser. No. 07/052,328, filed on May 21, 1987, now abandoned.

BACKGROUND OF THE INVENTION

This invention relates to the field of lipsomal immunoassays, and particularly to new substrates for immunoassays utilizing $\beta$-galactosidase.

In the assay of digoxin and other clinically important low concentration analytes which may be present in serum, especially human serum such as blood, using $\beta$-galactosidase-encapsulated liposomes, it is important to utilize an extremely sensitive chromogenic substrate in order to achieve the essential assay dynamic range. This is especially true when such an assay is performed on an automated analysis instrument such as, for example, a TECHNICON RA-1000 clinical chemistry analyzer. (TECHNICON RA-1000 is a registered trademark of Technicon Instruments Corporation, Tarrytown, NY.)

There are several known substrates for $\beta$-galactosidase, including: 2-methoxy-4-(2-nitrovinyl)-phenyl-$\beta$-D-galactopyranoside, which was disclosed as a substrate for the assay of $\beta$-galactosidase (C. T. Yuen, *Analytica Chimica Acta*, 163, (1982) 195–204); resorufin-$\beta$-D-galactopyranoside, which was disclosed as a fluorogenic substrate for $\beta$-galactosidase (*Analytica Chimica Acta*, 163, (1984) 67–72); E-1-1 (1-deoxylactulosyl)-2-lysine, which was disclosed as a substrate for determining the activity of $\beta$-galactosidase in the intestinal tract of mice (*J. of Chromatography*, 278, (1983) 275–282; and two high molecular weight substrates for $\beta$-D-galactosidase, each containing $\beta$-D-[3-H]-galactopyranosyl moieties linked through an aliphatic bridge to either poly-2-lysine or polymeric dialdehyde, which were disclosed by R. Madhan et al. (*Enzyme*, 25 (1980) 127–131).

The most common substrate for 62-galactosidase currently in use is O-nitrophenyl-$\beta$-D-galactopyranoside (ONPG) which is preferred for its relatively fast enzyme turnover rate, good stability in aqueous buffers and the relative ease by which it can be synthesized or commercially obtained. ONPG has a significant disadvantage, though, in that it has a relatively small molar absorptivity upon enzyme-catalyzed hydrolysis. Assays for digoxin and other clinically important low concentration analytes which utilize $\beta$-galactosidase encapsulated lipsomes require a more sensitive substrate to achieve the essential assay dynamic range.

Therefore, it is desired to produce a chromogenic substrate for $\beta$-galactosidase for use in the assay of digoxin and other clinically important low concentration analytes which may be present in serum such as blood, utilizing $\beta$-galactosidase-encapsulated liposomes. The substrate should be kinetically equivalent to known substrates such as ONPG and stable in aqueous buffers, but exhibit substantially increased molar absorptivity as compared to known substrates such as ONPG.

SUMMARY OF THE INVENTION

In accordance with the present invention, a substrate for $\beta$-galactosidase is provided which is of increased sensitivity and which is stable in aqueous buffers.

The invention provides a substrate for $\beta$-galactosidase which comprises a composition having the general formula

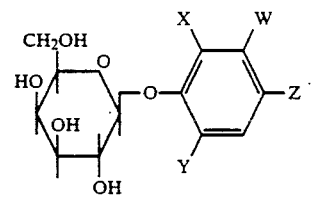

wherein X is halogen, nitro or hydrogen; Y is halogen, lower alkyl or hydrogen; W is lower alkyl or hydrogen; and Z is nitro or the following aromatic ring structure

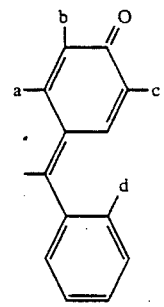

wherein a is lower alkyl or hydrogen; b is halogen or hydrogen; c is lower alkyl or hydrogen; and d is $SO_3Na$; and further wherein X is not nitro when Y is hydrogen.

BRIEF DESCRIPTION OF THE DRAWINGS

In the appended drawings, which are presented to further describe the invention and to assist in its understanding through clarification of its various aspects.

DETAILED DESCRIPTION OF THE INVENTION

Figure 1:
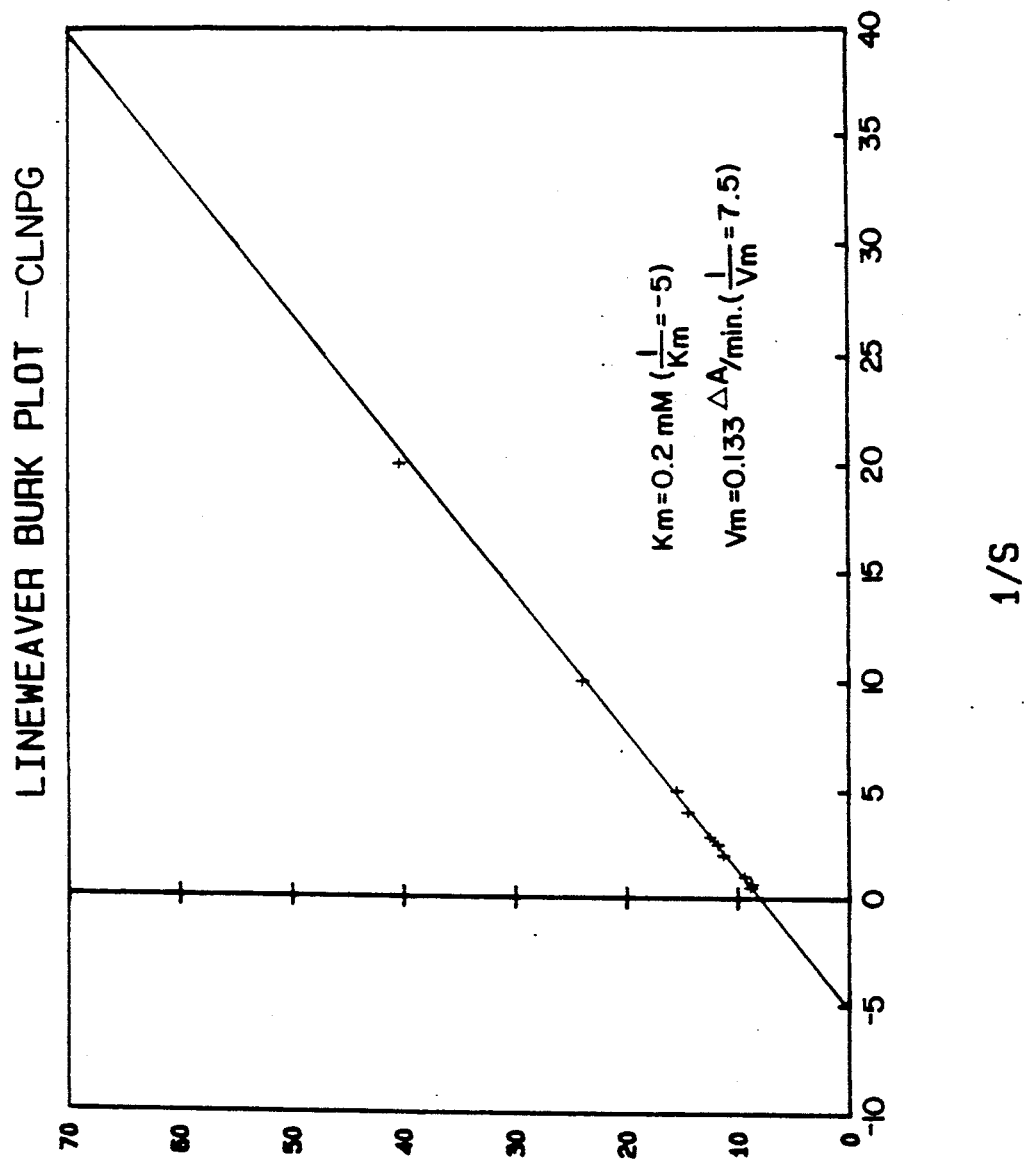
FIGS. 1 and 2 are Lineweaver an Burk plots for the preferred compound of the present invention.

For the purpose of this invention, the term "lower" means that the group described contains from 1 to 6 carbon atoms; the term "alkyl" refers to a straight or branched chain hydrocarbon containing no unsaturation, e.g., methyl, ethyl, isopropyl, 2-butyl, neopentyl, n-hexyl; the term "nitro" refers to the univalent group $NO_2$ having a free valence bond through nitrogen; the term "acetyl" refers to the univalent group $CH_3CO$ having a free valence bond; the term "halogen" refers to a member of the family consisting of fluorine, chlorine, bromine and iodine; the term "hapten" refers to any substance which does not stimulate antibody formation but reacts selectively in vitro with an antibody; and the term "serum" refers to any physiological fluid, such as blood.

The compositions of the present invention have the general formula (I)

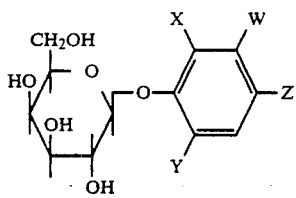 (I)

wherein X is halogen, nitro or hydrogen; Y is halogen, lower alkyl or hydrogen; W is lower alkyl or hydrogen; and Z is nitro or the following aromatic ring structure:

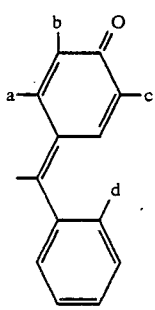

where a is lower alkyl or hydrogen; b is halogen or hydrogen; c is lower alkyl or hydrogen; and d is SO₃Na; and further wherein X is not nitrogen when Y is hydrogen.

The compositions of this invention are prepared in the following manner. The substituents W, X, Y, Z, a, b, c and d are as defined above unless indicated otherwise.

A compound of the formula (II)

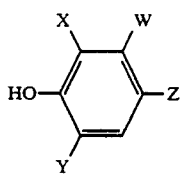 (II)

is reacted in a conventional manner with a galactopyranoside having formula (IIa)

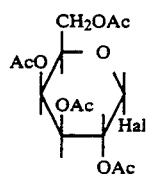 (IIa)

wherein Hal is halogen and Ac is acetyl, in a conventional manner under anhydrous conditions in the presence of K₂CO₃ and acetone for period of 36 hours, to form a compound of formula (III)

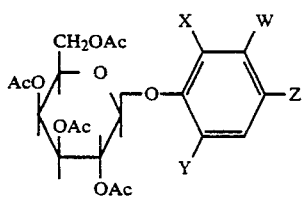 (III)

Compound III is then reacted in a conventional manner under anhydrous conditions in the presence of CH₃ONa and methanol for 36 hours to form compound I.

Preferably, the compositions useful as substrates for β-galactosidase are those in which: (i) X and Y are halogen, more preferably chlorine, W is hydrogen and Z is nitro (2,6-dichloro-4-nitrophenyl-β-D-galactopyranoside); (ii) X and Z are each nitro, Y is lower alkyl, more preferably methyl and W is hydrogen (2,4-dinitro-6-methylphenyl-β-D-galactopyranoside); (iii) X is halogen, more preferably bromine, Y is lower alkyl, more preferably methyl, W is hydrogen and Z is

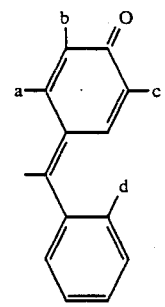

where a is hydrogen, b is halogen, more preferably bromine, c is lower alkyl, more preferably methyl, and d is SO₃Na (bromocresol purple); or (iv) X and Y are hydrogen, W is lower alkyl, more preferably methyl, and Z is

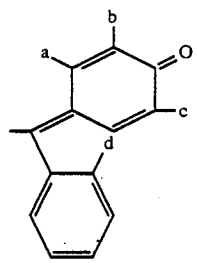

where a is lower alkyl, more preferably methyl, b is hydrogen, c is hydrogen and d is SO₃Na (metacresol purple).

The most preferred composition of this invention, 2-chloro-4-nitrophenyl-β-D-galactopyranoside (CLNPG), is one in which X is halogen, preferably chlorine, Y and W are each hydrogen and Z is nitro.

The compositions of this invention are useful as chromogenic substrates for β-galactosidase and are suitable for use in assays, especially immunoassays utilizing β-galactosidase. Typical applications for which the new substrate are exceptionally well suited include the use of antibody- or hapten-β-galactosidase conjugates in homogeneous and heterogeneous immunoassays in manual kit format or on analytical instruments such as the TECHNICON RA-1000 clinical chemistry analyzer or a TECHNICON CHEM-1 clinical chemistry analyzer. (TECHNICON CHEM-1 is a trademark of Technicon Instruments Corporation, Tarrytown, NY.). Protocols for such assays are conventional in the art and are known to the skilled artisan.

The hapten liposome immunoassay protocol adapted for use on the TECHNICON RA-1000 clinical chemistry analyzer is typical of such protocols and is summarized below:

| Samples | Reagent A | | Reagent B |
|---------|-----------|------|-----------|
| 30 ul | CLNPG substrate | 160 μl | liposome 35 |
| | Complement | 80 μl | |
| | PC | 40 μl | |
| | Buffer | 22 μl | |
| | Antibody | 48 μl | |
| | 4 minutes, 37° C. | | |
| | 5 minutes, 37° C. | | | wherein Complement refers to serum protein, PC refers to phosphocholine, a stabilizer, and the hapten-modified liposome 35 component is prepared by the following film deposition process. The membrane components consist of lecithin, sphingomyelin, tocopherol, dicetyl phosphate, cholesterol and hapten phospholipid conjugate. The membrane components are dissolved in chloroform solvent and evaporated on the inner surface of a one liter reaction vessel. The film is then hydrated with an aqueous buffer solution containing β-galactosidase, which is the entrapped enzyme marker, in the same reaction vessel. Liposomes spontaneously form in high yield. Separation of reagent liposomes from unentrapped enzyme is accomplished by ultracentrifugation.

The assay protocol involves the addition of sample and Reagent A into the reaction cuvette, incubation for 4 minutes, addition of Reagent B, and a second incubation of 5 minutes. Actual analyte concentrations are determined from a functionally linear standard curve from the calibrators.

The protocol outlined above was followed in Examples V and VI discussed below.

The following working examples describe experiments which were performed in developing the present invention. Standard commercially available reagent grade chemicals were used whenever possible. These examples are to be considered illustrative of the present invention and should not be interpreted as limiting its scope.

EXAMPLE 1

A. Synthesis of 2-chloro-4-nitrophenyl-2,3,4,6-tetra-o-acetyl-β-D-galactopyranoside To a solution of 2-chloro-4-nitrophenol, commercially available from Aldrich Chemical Company of Milwaukee, Wis., 43.39 gms. (0.25 mM) in 150 ml of acetone, was added 34.56 gms (0.25 mM) of anhydrous potassium carbonate to form a suspension. To this suspension was added 96.69 gms. (0.24 mM) of acetobromo-alpha-D-galactose to form a reaction mixture, which was heated to about 55° C. for 36 hours. The reaction mixture was monitored by thin layer chromatography (EM Silica gel 60 F254 in ethyl acetate/benzene [3/7 by volume]). The desired product ($R_f$=0.41) is detectable by short ultraviolet light as a brown spot after spraying with methanol/sulfuric acid (9/1 by volume) and heating at about 125° C. for 5 minutes. When the desired product was found, the reaction mixture was then cooled, filtered and evaporated with a water aspirator. The residue was dissolved in 40 ml of chloroform and washed with 1N cold sodium hydroxide and then with water. The combined organic layer was dried (using anhydrous sodium sulfate) and evaporated to dryness. The product was then crystallized from hot methanol to yield 91.94 gms of product (73%), having a melting point of 147°–149° C. Elemental Analysis: % C Actual 47.60 (Theoretical 47.67); % H 4.45 (4.41); % N 2.68 (2.78); % CL 6.91 (7.05); % O 38.02 (38.10).

B. Synthesis of 2-chloro-4-nitrophenyl-β-D-galactopyranoside (CLNPG)

1.0026 gms (1.99 mM) of the product of Example IA was suspended in dry methanol and a catalytic amount of anhydrous sodium methoxide (12 mg) was added to form a reaction mixture, which was maintained at 4° C. for 36 hours. The reaction mixture was monitored by thin layer chromotography [EM silica gel 60 F254 in chloroform/methanol (6/1 by volume], after which the reaction mixture was neutralized with acetic acid and the solvent evaporated. The residue was dissolved in hot methanol and a small amount (40 mg) of activated charcoal was added. The resulting mixture was then filtered to remove the charcoal and the filtrate was allowed to crystallize overnight. The crystals were then rinsed with ether and dried to yield 0.58 g of product (87%), having a melting point of 213°–215° C. and $R_f$ of 0.18. Elemental analysis % C, 42.65 (42.93); % H 4.06 (4.21); % N 3.92 (4.17); % Cl 10.82 (10.56); % O 38.17 (38.13).

EXAMPLE II

The molar absorptivity ($\epsilon_{max}$) of the phenolic precursers of several compositions of this invention were measured and calculated according to the following formula:

$$\epsilon_{max} = \frac{A}{c \times b}$$

wherein A is the absorbance; b is the path length through the sample; and c is the cocentration of solute.

The molar absorptivity of the phenolic precurser of ONPG, the most commonly used prior art substrate for β-galactosidase was likewise measured and calculated for comparative purposes. The aim was to identify phenolic precursors which would provide enhanced molar absorptivity to that of ONPG.

The results are set out in Table I.

TABLE I

| Phenol | Molar Absorptivity (ε max) |
|--------|----------------------------|
| bromocresol purple | 50.7 (585 nm, pH 8.5) |
| 2-chloro-4-nitrophenol (CLNP) | 16.9 (405 nm, pH 7.5) |
| 2,6-dichloro-4-nitrophenol | 15.9 (405 nm, pH 7.5) |
| 2-chloro-4,6-dinitro phenol | 11.5 (405 nm, pH 7.5) |
| 2,4-dinitro-6-methyl phenol | 11.0 (405 nm, pH 7.5) |
| 2,4-dinitro phenol (DNP) | 10.7 (405 nm, pH 7.5) |
| metacresol purple | 8.4 (575 nm, pH 8.5) |
| 2-chloro-6-nitrophenol | 4.6 (405 nm, pH 7.5) |
| orthonitro phenol (ONP) | 3.0 (405 nm, pH 7.5) |

These calculations clearly show that the compositions of the present invention display relatively high molar absorptivity, which relates to the chromogenic characteristics of the composition upon chemical and enzymatic hydrolysis, especially when compared to the preferred prior art composition.

EXAMPLE III

One object of the present invention was to provide a new substrate for β-glactosidase which has a higher enzymatic rate than the preferred prior art composition.

The mechanism of one substrate enzymatic reaction can be represented as follows:

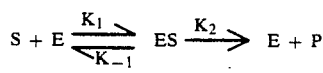

wherein S is substrate, E is enzyme, P is product, $K_1$ and $K_2$ are the rate constants for the forward reaction, and $K_{-1}$ is the rate constant for the reverse reaction.

The detailed discussion of the chemical reaction kinetics is presented in "Principles of Enzymatic Analysis" edited by Hans Ulrich Bergmeyer in collaboration with Karlfried Gamehn 1978, Verlag Chemie.

Various kinetic parameters of the enzyme reaction were measured including Km, Vmax and Kp.

Km is the Michalis constant. It expresses the substrate concentration at which the reaction rate has half of its maximum value.

$$K_m = \frac{K_{-1} + K_2}{K_1}$$

$K_m$ is by no means an absolute constant, but depends on pH, temperature, effectors, buffers, etc. The reaction conditions should therefore always be specific in connection with the Km value.

The reaction rate can be expressed as $$v = \frac{V}{1 + Km/S}$$

The most commonly used method for calculation of Km is that of Lineweaver and Burk.

$$\frac{1}{v} = \frac{Km}{V} \cdot \frac{1}{[S]} \cdot \frac{1}{V}$$

This is the equation of a straight line (1/v plotted against 1/[S]), corresponds to $y = ax + b$.

Insertion of y=o gives ax=−b, −x=b/a. In this case for 1/u=o (i.e., intercept on the abscissa), [S]=Km. If x=o, then y=b. In this case: for 1/[S]=o (i.e., intercept on the ordinate), 1/v=1/V.

Both important characteristics of an enzyme (Km and V max) are thus obtainable in a single operation Kp is the turnover number which is easily obtained if V max ($V_m$) and enzyme concentration (Ec) are known. Kp is expressed as Kp=Vm/Ec.

Figure 2:
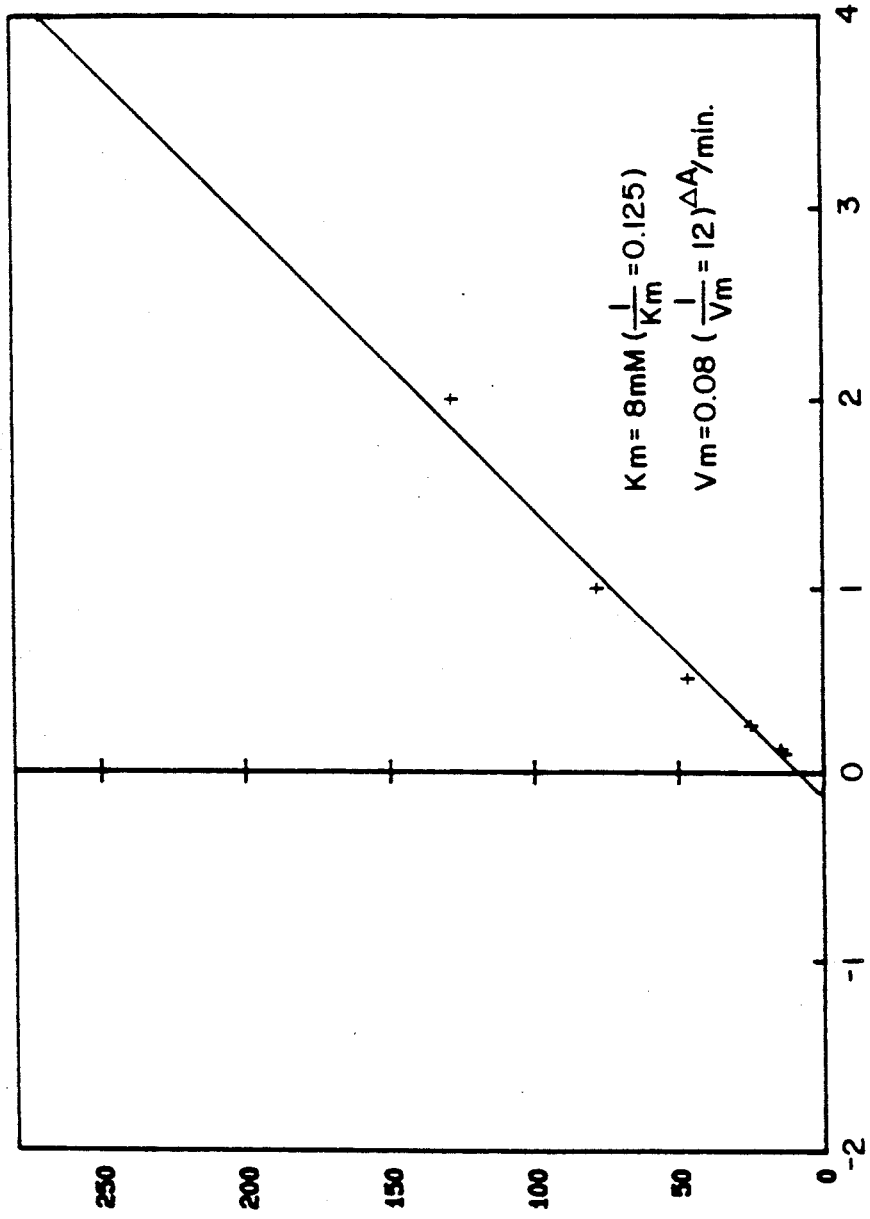

Calculated values of Km, V max and Kp for certain compositions of the present invention, CLNPG and BCPG, are based on experimental data plotted in FIGS. 1 and 2 respectively, and appear in Table II as do values for ONPG and DNPG which are available from the literature.

TABLE II

| Substrate | Km (mM) | V max (ΔA/Min) | Kp (Vm/Ec, Min$^{-1}$) |
|---|---|---|---|
| 2-chloro-4-nitro-phenyl-β-D-galactopyranoside (CLNPG) | 0.20 | 0.13 | $7.40 \times 10^4$ |
| bromocresol purple-β-D-galactopyranoside (BCPG) | 8.0 | 0.11 | $3.10 \times 10^2$ |
| orthonitrophenyl-β-D-galactopyranside (ONPG) | 0.17 | 0.03 | $1.82 \times 10^5$ |
| 2,4-dinitro-phenyl-β-D-galactopyranoside (DNPG) | 0.22 | 0.13 | $2.20 \times 10^5$ |

The advantage of the preferred composition of this invention CLNPG (2-chloro-4-nitrophenyl-β-D-galactopyranoside) over ONPG, the preferred prior art composition, in terms of V max which relates to the maximum enzymatic rate, is evident from the above. While the Km and Kp parameter of both compositions are similar, the V max of CLNPG is at least four times that of ONPG. DNPG, while showing good kenetic parameters is unstable in aqueous environment.

EXAMPLE IV

The enzymatic response of 2-chloro-4-nitrophenyl-β-D-galactopyranoside (CLNPG) was measured and compared with that of ortho-nitrophenyl-β-D-galactopyranoside (ONPG) by the following free enzyme protocol performed on a TECHNICON RA-1000 clinical chemistry analyzer:

15 ul of known concentration of β-galactosidase in buffer (1 mg/ml) was added to 300 ul of substrate (2.5 mM in buffer). The buffer used was 50 mM Tris HCl and 150 mM NaCl and 5 mM MgCl$_2$ (pH 7.5). The enzymatic reaction product was measured at 405 nM after 30 seconds and the Δ A 405 nm/min for three different concentrations of β-galactosidase was recorded for each substrate. The results are shown in Table III.

TABLE III

| β-galactosidase concentration | Δ 405/min. (CLNPG) | Δ 405/min. (OPNG) | Ratio (CLNPG/ONPG) |
|---|---|---|---|
| 0 | .0007 | .0003 | — |
| 1/2000 | .0427 | .0077 | 5.5 |
| 1/1000 | 0.0923 | 0.0159 | 5.8 |
| 1/200 | 0.4555 | 0.0795 | 5.7 |

EXAMPLE V

The enzymatic response rate of 2-chloro-4-nitrophenyl-β-D-galactopyranoside (CLNPG) was measured and compared with that of orthonitrophenyl-β-D-galactopyranoside (ONPG) by the following β-galactosidase encapsulated liposome protocol performed on a TECHNICON RA-1000 clinical chemistry analyzer:

15 ul of liposome was added to 300 ul of substrate (2.5 mM in buffer) and mixed for 30 seconds. The buffer used was 0.05M Tris HCl and 150 mM NaCl and 5 mM MgCl$_2$ (pH 7.5). The enzymatic rate of the mixture was then measured at 405 nm (−T). For chemical lysis, the identical mixture was prepared but 0.1% Triton X-100 was substituted for the buffer. The enzymatic rate of the mixture was measured at 405 nm (+T). The 405 nm/min [(+T) −(−T)] for three different concentrations of liposome was recorded for each substrate. The results are shown in Table IV.

TABLE IV

| β-galactosidase-encapsulated liposome concentration (1/20 Dilution) | Δ 405/min (CLNPG) | Δ 405 nm/min (ONPG) | CLNPG/ONPG |
|---|---|---|---|
| 0.1 | 0.0180 | 0.0030 | 6.0 |
| 0.5 | 0.0915 | 0.0138 | 6.6 |
| 1.0 | 0.1803 | 0.0279 | 6.5 |

EXAMPLE VI

Figure 3:
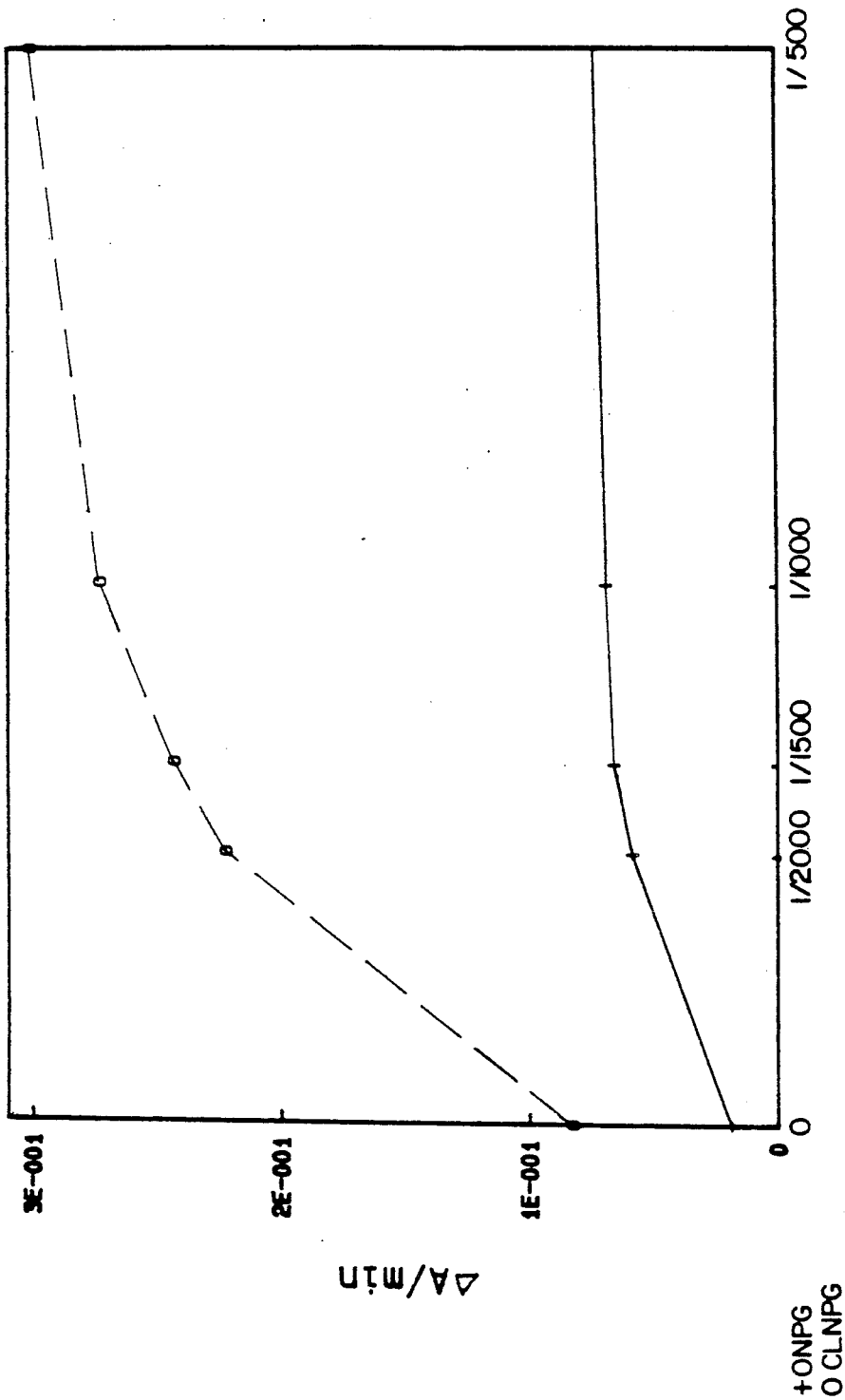
FIG. 3 is a diogxin immunoassay—antibody titration curve comparing the performance of the preferred compound of the present invention to that of the preferred prior art compound.

A digoxine liposome immunoassay was performed by using the above-mentioned protocol to compare the utilizing of CLNPG and ONPG. The antibody titration curve, as shown in FIG. 3, clearly illustrates that the performance of CLNPG was superior to that of ONPG, the former offering a four-fold increase in assay sensitivity over the latter for a wider range of antibody.

It is apparent from the above that the use of the preferred substrate of this invention in both free enzyme and β-galactosidase-encapsulated liposome assays allows for an assay at least 5 times as sensitive as current prior art assays.

It should be understood by those skilled in the art that various modifications may be made in the present invention without departing from the spirit and scope thereof as described in the specification and defined in the amended claims.

What is claimed is:

1. A substrate for β-galactosidase comprising a compound of the formula

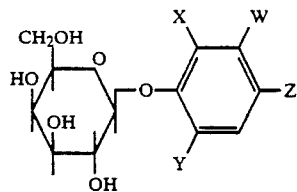

wherein X is halogen; Y is halogen, lower alkyl or hydrogen; W is hydrogen or lower alkyl; and z is nitro.

2. The substrate of claim 1 wherein X is chlorine.
3. The substrate of claim 1 wherein X is bromine.
4. The substrate of claim 1 wherein Y is halogen.
5. The substrate of claim 4 wherein Y is chlorine.
6. The substrate of claim 1 wherein Y is lower alkyl.
7. The substrate of claim 6 wherein Y is methyl.
8. The substrate of claim 1 wherein W is lower alkyl.
9. The substrate of claim 8 wherein W is methyl.
10. The substrate of claim 1 wherein X is halogen; Y is hydrogen; W is hydrogen and Z is nitro.
11. The substrate of claim 10 wherein X is chlorine.
12. The substrate of claim 1 wherein Y is halogen; W is hydrogen; and Z is nitro.
13. The substrate of claim 12 wherein X is chlorine.
14. The substrate of claim 12 wherein Y is chlorine.
15. The substrate of claim 13 wherein X and Y are both chlorine.
16. The substrate of claim 1 wherein Z is nitro; Y is lower alkyl; and W is hydrogen.
17. The substrate of claim 16 wherein Y is methyl.
18. A method for determining the presence of an analyte in a test sample by enzyme immunoassay when said enzyme reagent is β-galactosidase comprising the steps of (a) providing a test sample suspected of containing the analyte to be determined;

(b) reacting said test sample with a first reagent comprising an antibody to said analyte, a substrate, and a second reagent comprising an enzyme conjugate reactive either with the antibody or the analyte and capable of generating a detectable response in the presence of said substrate; and (c) determining the presence of said analyte as a result of the detectable response generated by the interaction of said enzyme and said substrate; wherein the improvement comprises using as said substrate of step (b) a compound of the formula

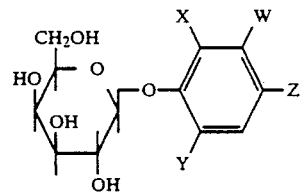

wherein X is halogen; Y is halogen, lower alkyl or hydrogen; W is hydrogen or lower alkyl; and Z is nitro.

* * * * *